United States Patent [19]

Eschweiler et al.

[11] 4,397,639
[45] Aug. 9, 1983

[54] DEVICE FOR THE INTERMITTENT PULSATORY APPLICATION OF FLUID MEDICAMENTS

[75] Inventors: Wilhelm Eschweiler, Rammsee; Gerhard Leyendecker, Bonn-Bad-Godesberg, both of Fed. Rep. of Germany

[73] Assignee: Ferring Arzneimittel GmbH, Kiel, Fed. Rep. of Germany

[21] Appl. No.: 256,725

[22] Filed: Apr. 23, 1981

[30] Foreign Application Priority Data

Apr. 24, 1980 [DE] Fed. Rep. of Germany ....... 3015777

[51] Int. Cl.³ .............................................. A61M 5/00
[52] U.S. Cl. ........................... 604/153; 128/DIG. 12; 417/234; 417/411; 417/477
[58] Field of Search ............. 128/214 E, 214 F, 214.2, 128/273, DIG. 12; 417/53, 234, 476, 477, 411; 604/153

[56] References Cited

U.S. PATENT DOCUMENTS 3,582,234  6/1971  Isreeli et al. .......................... 417/53
4,006,743  2/1977  Kowarski ..................... 128/214.4 X
4,078,562  3/1978  Friedman ........................ 128/214 F
4,150,672  4/1979  Whitney et al. ................ 128/214 F

FOREIGN PATENT DOCUMENTS 2851656  6/1979  Fed. Rep. of Germany ... 128/214 F
WO81/01728  6/1981  PCT Int'l Appl. ................. 417/477

Primary Examiner—Dalton L. Truluck
Attorney, Agent, or Firm—Pearne, Gordon, Session, McCoy, Granger & Tilberry

[57] ABSTRACT

A device for the intermittent pulsatory application of fluid medicaments, particular for the application of LH-RH for initiating ovulation in women having hypothalamic and hyperprolactinamic amenorrhea. Said device has a reservoir for the medicament and a hose connected to said reservoir for delivering said medicament to a patient, which reservoir and which hose are a prefabricated unit which can be inserted into the device and removed when the content of the reservoir is exhausted. Furthermore, said device has a roller-type pump acting onto said hose when it is stretched onto the needle-like rollers of said roller-type pump, and a D.C. motor for driving said pump and further control means for controlling said motor, said control means having a timer for pulse and pause times so that the motor is energized only for short periods not longer than several minutes while it is between each two of such running periods stopped for more than one hour. At least one battery is provided as energy source for the D.C. motor.

15 Claims, 3 Drawing Figures

DEVICE FOR THE INTERMITTENT PULSATORY APPLICATION OF FLUID MEDICAMENTS

FIELD OF THE INVENTION

The invention relates to a device for the intermittent pulsatory application of fluid medicaments, particularly for the application of LH-RH for initiating ovulation in women having hypothalamic and hyperprolactinamic amenorrhea.

BACKGROUND OF THE INVENTION

In patients having hypothalamic and hyperprolactinamic amenorrhea the best treatment results are obtained when the pulsation of the natural secretion of LH-RH is simulated at intervals of 90 minutes between the individual doses of the medicament to initiate ovulation.

It is known to feed metered quantities of fluid and/or gaseous medicaments by means of devices which are driven by electric motors and which are provided with means for interchangeable programmes. A mechanically controlled device for continuous infusion of medicaments is disclosed in Austrian Pat. No. 210 558. Furthermore, German Auslegeschrift No. 1 491 747 discloses an injection device for single injection of a roentgen contrast agent, wherein the injected quantity, the rate and, if required, a time delay can be controlled by means of an electrical programme transmitter.

For performing diabetes therapy an application device is known from German Auslegeschrift No. 2 451 424 which comprises a programmable control of an electric motor for actuating a syringe over a longer time period. Another infusion device for diabetes therapy described in German Offenlegungsschrift No. 2 758 368 is provided with an external programming device, an electrical control means and a micro-metering unit. These two known devices operate with a long-term programme and have, if required, infusion rate switches.

Furthermore, portable infusion devices for the infusion of fluids are known which comprise a removable reservoir for the fluid and a roller-type pump as feeding and metering unit for feeding the infusion fluid from the reservoir to the discharge opening of a catheter (compare German Offenlegungsschriften DE-OS Nos. 29 20 975, 26 52 026 and 26 51 962). These known devices are for instance very small and have such low weight that they are implantable or, alternatively, can be carried on the patient's body without hindering the patient. Since they are to be used for diabetes therapy, the quantity of fluid infused is programmable in different rates and is programmable in cycles of days, the flow rates being in the order of magnitude of microliters per hour ($10^{-6}$ l/h). Also, switching means for monitoring and/or connecting the volume of fluid fed from the roller-type pump to the discharge end of the catheter are provided. However, exchanging the reservoir is complicated, especially because it is difficult to position that part of the catheter or hose which cooperates with the roller-type pump between the head portion of the pump and a fixed jaw. Therefore, these known infusion devices are in the praxis not suitable for the intermittent pulsatory application of fluid medicaments, especially of fluid LH-RH medicaments.

OBJECT OF THE INVENTION

The object of the invention is to provide a device for the intermittent application of fluid medicaments which feeds the medicament and especially LH-RH medicament impulses of predetermine intervals by means of an electrically driven roller-type pump from a removable reservoir through a discharge catheter for instance into the vein of a patient's forearm. Preferably, the reservoir should be removable and insertable in simple and quick manner.

DETAILS OF THE INVENTION

The device of the present invention comprises a prefabricated reservoir of certain dimensions having a flexible hose for discharging the fluid medicament from said reservoir, wherein the control means for the motor driving the roller-type pump has a timer for impulse and pause times. The motor is a D.C. motor, and at least one battery is provided as energy source for said motor. The timer for the impulse and pause times comprises preferably of a timing generator, a frequency divider and a driver stage which are connected in series.

By means of such control the drive of the D.C. motor is adjusted to pause times in the order of hours and to running times in the order of minutes, so that for instance each ninety minutes a single dose of the medicament can be applicated to the patient. By means of a special switching contact the drive motor can be energized at every desired time arbitrarily, while the control means can be set to zero by a reset button.

In this system the operation cycle for the impulse sequence cannot be varied. It is sufficient that the treatment can be extented over various periods of time.

It is a certain feature of the present invention that the hose for feeding the fluid medicament is provided between the reservoir and the discharge end in a predetermined distance with two stretching elements like two collars or two sockets, the portion between these two stretching elements being that portion of the hose which is passing the head portion of said roller-type pump. The two stretching elements can be positioned behind openings or the fixed wall so that the flexible hose or flexible catheter can be stretched over said head portion so that the needle-like rollers of said head portion act onto the hose as pumping means when the pump is operated and its head portion rotated around its axis. Therefore, no fixed jaw for cooperating with the head portion of the roller-type pump is necessary as in the known devices of this kind so that the flexible hose or flexible catheter is easily and quickly to be inserted and can also be removed easily and quickly.

The advantages obtained by the invention reside in the fact that the quantity of medicament, particularly the LH-PH dissolved in a carrier or vehicle, prescribed by the physician can be administered ambulantly to a patient in the rhythm recognised to be natural. The device is portable on the patient's body and can be used repeatedly because the medicament is provided in a removeable closed container-hose system so that there are no medical objections with respect to the sterility of the medicament during administration.

DESCRIPTION OF THE DRAWINGS

One embodiment of the device of the present invention is schematically illustrated in the accompanying drawings, in which.

Figure 1:
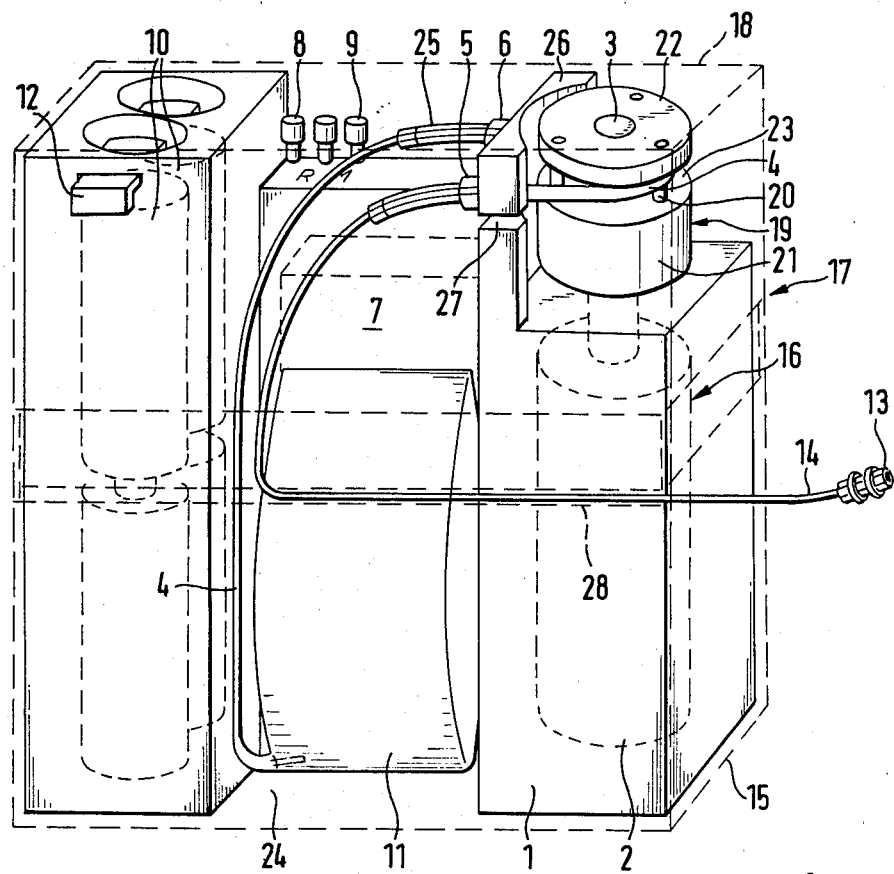
FIG. 1 is a perspective view of the device arranged in a housing.
Figure 2:
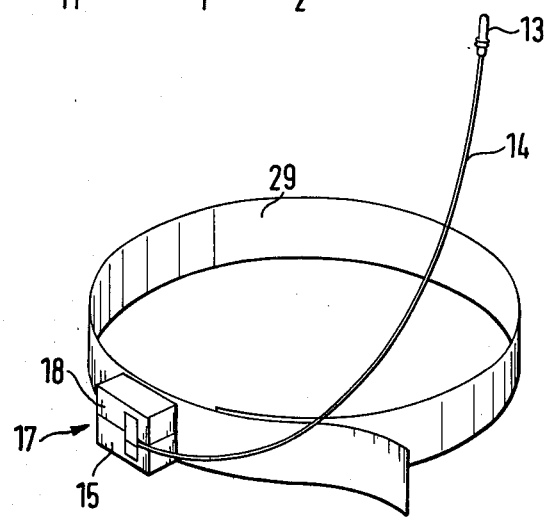
FIG. 2 is a perspective view of the portable device attached to a belt, in smaller scale than in FIG. 1, and FIG. 3 a block circuit diagram of the controlling means for this device.

The device is illustrated in FIG. 1 in an enlarged scale to clearly show the details thereof while it is illustrated in FIG. 2 smaller than in its actual size.

In a block-like frame 1 a roller-type pump 16, an electronic controlling means 7 for controlling the roller-type pump 16 and electric batteries for feeding D.C. as energy source for driving the roller-type pump 16 are provided. The block-like frame 1 is inserted into the lower portion 15 of a box-like housing 17, the cover portion 18 of said housing being removable so that the upper portion of the block-like frame 1 can be exposed.

The roller-type pump 16 has a D.C. driven motor 2 with a driven shaft 3 on which a head portion 19 is fixed so that it is rotated with shaft 3. Parallel to the axis of head portion 19 and shaft 3 are arranged within head portion 19 needle-like rollers 20 which extend between a disk 21 and a cover disk 22 so that these rollers 20 are provided in a guiding slot 23.

In a recess 24 of the block-like frame 1 is inserted a removable flexible reservoir 11 of standardized size (i.e. a size available in the trade) to which as discharging means a flexible hose 4 is connected, which hose extends through the slot 23 of the head portion 9 of the roller-type pump 16. At the discharge end of hose 4 a catheter 14 with a connection piece 13 is provided. Hose 4 extends through a hose-like elastic sleeve 25 which is shown in FIG. 1 only partly. On the outer surface of sleeve 25 are fixed in a predetermined mutual distance to nipple-like collars 5 and 6. These collars 5 and 6 are positioned behind an upstanding wall 26 of frame 1, which wall is provided at its opposing sides with lateral horizontal slots 27 into which the elastic extensible hose 4 and sleeve 25 are inserted so that their portion between the collars 5 and 6 is laid around the head portion 19 of the roller-type pump 16 and is stretched against the needle-like rollers 20. Therefore, in operation the individual rollers 20 cooperate with the stretched hose 4 as pumping means.

The catheter 14 which is the one end of hose 4, is clamped into a groove 28 which is provided in the front side of frame 1 so that it cannot be displaced if not desired. On the other hand, the groove 28 is wide enough to avoid that the lumen of the inserted catheter 14 is reduced.

Even though the hose-like sleeve 25 is shown in FIG. 1 only partly it is to be understood that this sleeve can extend nearly over the entire length of hose 4 so that it effectively protects the very fine hose 4 against damages.

Motor 2 is a D.C. motor which is energized by the batteries 10 and controlled by an electronic control means 7 which is a control circuit. By means of a press button switch 8 motor 2 can be energized independent of the programme of control means 7 at any time when desired. By actuating a reset button 9 the electronic control means 7 can at any time be set to zero so that the programme sequence starts again from the beginning.

A contact slide 12 cooperates with the upper ends of four batteries 10 under operational conditions. This tongue-like contact slide 12 is made preferably of spring steel. If it is removed, the circuit is interrupted so that no electric current is delivered from the batteries and the batteries are not exhausted unnecessarily.

In FIG. 2 is shown that the device is attached to the outer side of a belt 29 so that it is easily portable on the body of a patient.

Figure 3:
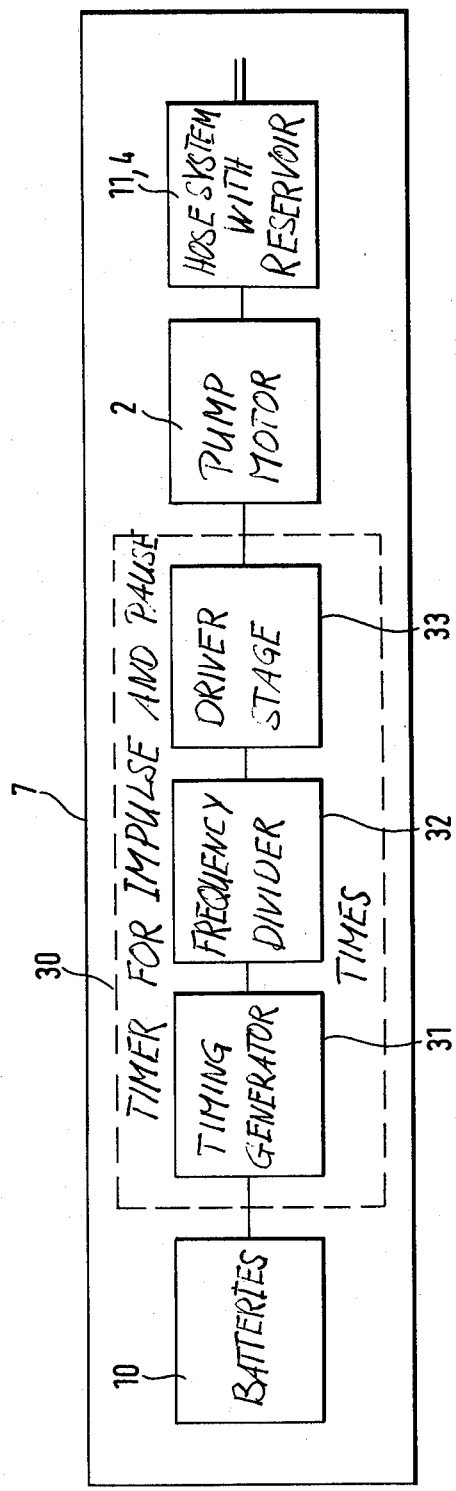

The electronic control means 7 comprises, as shown in FIG. 3, a timer 30 which measures pause or interruption times in hours and which can be set for interruption time between 1 to 99 hours. Furthermore, the timer 30 measures impulse times and thus also infusion times, which times can be set between one to nine minutes. The timer 30 comprises of a timing generator 31, a frequency divider 32 and a driver stage 33 which are connected in series and serve as the timing unit so that the electric current flows from the batteries 10 through this timing unit to motor 2 for driving the roller-type pump 16.

The device operates as follows:

First of all, a reservoir 11 which contains a fluid medicament is inserted into the recess 24, and hose 4 is laid around the head portion of the roller-type pump 16 and is stretched against this head portion. Then, reset button 9 is pressed to set the electronic control means 7 to zero. To test the function of the roller-type pump 16 the press button switch 8 is now actuated. Thus, motor 2 is switched on and runs as long as press button switch 8 is pressed down. By the rotation of the driven shaft 3 of motor 2 within this impulse time the needle-like rollers 20 circulate so that the fluid within the stretched part of hose 4 is fed into catheter 14 and to the connection piece 13 where it is discharged for instance into the vein in one forearm of the patient.

Reservoir 11, hose 4 and catheter 14 with its connection piece 13 are a prefabricated sterile disposable unit of predetermined standardized size which is disposed of or discarded when the medicament in reservoir 11 is exhausted. Those parts of this unit which come into contact with the medicament are made of polyethylene while hose 4 is preferably made of silicon. This sterile unit is supplied in a sterile form to the physician who inserts it to the device and starts operation of the device to administer the medicament to the patient.

The housing 17 is for instance a rectangular box with a base area of 100×20 mm and a height of 50 mm. Therefore, it is easily portable by means of a belt 29 on a patient's body.

The timer 30 of the electronic control means 7 measures pause times of the device in hours which are set for instance for one and a half hours, and also measures the pulse times which are set for example to one minute. In this operational cycle the control means 7 controls the operation of motor 2 during the relatively short pulse times of for instance one minute while between two of those pulse times the operation of the motor is interrupted for long periods of for instance one and a half hours.

What we claim is:

1. A portable apparatus adapted to be worn by a patient user for the intermittent pulsatory application of fluid medicament comprising: a disposable reservoir and hose assembly including a flexible reservoir container for medicament, a hose communicating between the reservoir container and a hose pumping portion having its discharge end in fluid communication with a catheter; a roller-type pump means including a a head portion rotatable about an axis of rotation and having angularly spaced rollers adapted to act on said hose pumping portion; a D.C. motor for driving said pump means; control means for controlling said motor including a timer for pulse and pause times; battery means for supplying electrical energy to said motor, and an openable housing and a frame cooperating to enclose and mount the pump means, motor, control means, battery means, and reservoir and hose assembly with said catheter extending from said housing for delivery of the medicament to a patient; said housing and frame cooperating to provide a recess for receiving said reservoir container and a pair of hose mounts for removably mounting said reservoir and hose assembly; a collar fixed to each end of said hose pumping portion; each of said collars being adapted to be resiliently biased into engagement with an associated one of said hose mounts with said hose pumping portion extended elastically through said hose mounts and tensioned against said rollers; said hose pumping portion, hose mounts and rollers being visible and directly accessible upon opening of said openable housing to enable insertion and removal of said reservoir and hose assembly without further disassembly of said apparatus.

2. An apparatus as set forth in claim 1, wherein said hose mounts comprise wall openings provided by said frame, said openings being sized to pass said hose pumping portion and to restrain said collars as they are resiliently biased into engagement with the adjacent wall portions.

3. An apparatus as set forth in claim 1, wherein said hose mounts comprise elongated wall slots adapted to receive said hose pumping portion and to interfere with said collars.

4. An apparatus as set forth in claim 3, wherein said frame includes a block element for mounting said pump means within said housing, said block element includes a wall adapted to extend between said head portion and said flexible reservoir container, and said elongated wall slots are provided in said wall.

5. An apparatus as set forth in claim 1, wherein said frame includes a block element, said pump means, motor, control means and battery means are mounted to said block element, said block element is fitted within a lower portion of said openable housing, and said block element is substantially coextensive with the interior region of said housing.

6. An apparatus as set forth in claim 1, wherein said hose pumping portion is adapted to extend in a single wrap around said head portion of said pump means, and said head portion includes a circumferentially extending guiding slot adapted to receive said hose pumping portion when the hose pumping portion is tensioned against said rollers.

7. An apparatus as set forth in claim 6 wherein said hose mounts are provided by said frame and comprise elongated slots extending through a wall of said frame, said slots are adapted to pass said hose pumping portion and to restrict said collars, said slots and said head portion of said pump means are located adjacent the top of said frame, and said housing includes a top cover which is removed when the housing is opened.

8. An apparatus as set forth in claim 7, wherein said guiding slot in said head portion has a depth which is greater than the diameter of said pumping portion.

9. An apparatus as set forth in claim 7, wherein said head portion includes a pair of axially spaced discs having said rollers axially extending therebetween, said discs and rollers cooperating to provide said guiding slot.

10. An apparatus as set forth in claim 1, wherein said hose pumping portion includes a silicone hose.

11. An apparatus as set forth in claim 10, wherein said silicone hose is an elastic protective sleeve.

12. An apparatus as set forth in claim 1, wherein said timer comprises a timing generator, a frequency divider and a driver stage which are connected in series.

13. An apparatus as set forth in claim 1, wherein a speed reducer means is provided between said motor and said roller-type pump means.

14. An apparatus as set forth in claim 1, wherein said control means operates to cause said motor to run not longer than several minutes while it is stopped between two running periods for more than one hour.

15. An apparatus as set forth in claim 1, further having a switch means for manually starting said motor when desired and a reset button for setting said control means to zero when said motor is started manually.

* * * * *